United States Patent [19]

Takahama et al.

[11] Patent Number: 5,281,915

[45] Date of Patent: Jan. 25, 1994

[54] SENSOR FOR DETECTING A HIGH MOLECULAR WEIGHT SUBSTANCE USING IONIZATION EFFECTS

[75] Inventors: Teizo Takahama; Ryuji Hanafusa; Yoshiteru Yoshida, all of Kawasaki, Japan

[73] Assignee: Fuji Electric Co., Ltd., Kawasaki, Japan

[21] Appl. No.: 870,266

[22] Filed: Apr. 17, 1992

[30] Foreign Application Priority Data

Apr. 22, 1991 [JP] Japan .................. 3-90418
Aug. 28, 1991 [JP] Japan .................. 3-215643

[51] Int. Cl.$^5$ ................ G01N 27/62; G01N 27/64; H01J 47/02
[52] U.S. Cl. .................. 324/464; 324/469; 73/31.05; 250/283
[58] Field of Search .............. 324/464, 469, 459; 73/23.2, 31.05; 250/283, 287, 382

[56] References Cited

U.S. PATENT DOCUMENTS

| | | | |
|---|---|---|---|
| 3,087,113 | 4/1963 | Foster | 324/464 |
| 3,835,328 | 9/1974 | Harris et al. | |
| 3,986,111 | 10/1976 | Sellers | |
| 4,075,550 | 2/1978 | Castleman et al. | 324/464 |
| 4,119,851 | 10/1978 | Castleman et al. | |
| 4,238,678 | 12/1980 | Castleman et al. | |
| 4,724,394 | 2/1988 | Langer et al. | 73/31.05 |
| 4,769,540 | 9/1988 | Mitsui et al. | |
| 4,775,795 | 10/1988 | Biehl et al. | |
| 4,777,363 | 10/1988 | Eiceman et al. | |

FOREIGN PATENT DOCUMENTS

| | | |
|---|---|---|
| 0253155 | 1/1988 | European Pat. Off. . |
| 2198579 | 6/1988 | United Kingdom . |
| 2228139A | 6/1990 | United Kingdom . |
| 87/07720 | 12/1987 | World Int. Prop. O. . |

*Primary Examiner*—Gerard R. Strecker
*Assistant Examiner*—Diep Do
*Attorney, Agent, or Firm*—Spencer, Frank & Schneider

[57] ABSTRACT

A small, light and portable sensor for detecting and quantifying a harmful high molecular weight substance present in a sample gas in trace amounts is herein disclosed. In the sensor, light and heavy ions are formed by ionizing molecules of the sample gas components in an ionization region. The heavy ions are formed through an ion-molecule reaction. The passage of ions through an ion-passage control region is controlled by directly or indirectly controlling the electric field established between a central electrode and a counter electrode The ions which pass through the control region are collected on a collector electrode. The high molecular weight substance is detected and quantified on the basis of the output from the collector electrode.

16 Claims, 6 Drawing Sheets

SENSOR FOR DETECTING A HIGH MOLECULAR WEIGHT SUBSTANCE USING IONIZATION EFFECTS

BACKGROUND OF THE INVENTION

1. Field of the Invention

The present invention relates to a sensor for detecting a high molecular weight substance present in a low molecular weight gas such as air, and more particularly to a sensor which can be used in environmental and medical measurements or semiconductor manufacturing processes for monitoring a trace amount of a harmful high molecular weight substance present in air or other low molecular weight gas, the sensor being highly sensitive, compact and lightweight and being convenient for portable use.

2. Description of the Prior Art

An example of an apparatuses used for detecting high molecular weight substances present in the air is disclosed in U.S. Pat. No. 4,769,540. The apparatus disclosed in this patent is based on the atmospheric ionization mass spectrometric method. This method comprises the steps of ionizing molecules of the air to yield light ions, ionizing a polymeric substance present in the air through an ion-molecule reaction between the light ions and the high molecular weight substance to thus yield heavy ions, and then guiding these light ions and heavy ions to a mass spectrometer to quantitatively analyze the heavy ions. In this first conventional apparatus, however, the path through which these ions are transported must be maintained at a high vacuum in order to separate the ions from each other and obtain correct mass spectra. Since a high vacuum pump is needed, such an apparatus cannot be installed at any desired place, and furthermore carrying the apparatus and using it for onsite measurements is cumbersome.

Another known method comprises the steps of forming light and heavy ions as in the foregoing conventional apparatus, extracting ions by applying a pulse voltage to a grid disposed perpendicularly to the direction of flow of the air containing these ions, and separating and determining the heavy ions according to the atmospheric ionization flight time measuring method. This method makes use of the difference in time for the light and heavy ions to arrive at the grid after the application of the pulse voltage, since the flight velocity of the light ions differs from the that of the heavy ions. In this method, however, the effective flight time separation of masses is ensured only when the ionization chamber is as small as possible so as to restrict, to a narrow region, the flight-initiation position of the ions attracted to the grid through the application of the pulse voltage. For this reason, it is necessary to use only radiation emitted toward a specific direction obtained through the collimation of the radiation emitted from a source such as $^{63}$Ni, which emits radiation having a short trajectory. This greatly restricts the resulting ionization efficiency. In addition, the effective time which is available for the measurement is greatly limited by the time interval of the pulse-voltage application. Furthermore the use of a source (e.g., $^{63}$Ni, 50 mCi) which emits very strong radiation would be severely restricted by regulations on the handling of radioactive substances.

GB 2,228,139A discloses an improved ion-mobility-detector based on the atmospheric ionization flight time measuring method. This detector comprises an ion source disposed at a position branching off from a ion reaction region, at least two drift regions which communicate with the ion reaction region, an electrical ion injection shutter disposed between the ion reaction region and each drift region, and an ion detector positioned at the end of each drift region far apart from the ion reaction region. In each drift region, a potential gradient is established so as to define the drift direction of the ions. The detection of ions in a sample gas is performed on the basis of the lapse of time from the opening of the ion injection shutters till the ions are detected by the ion detectors, or on the basis potential applied to the ion source and the timing of an opening pulse applied to the ion injection shutters is adjustable. This apparatus makes it possible to perform separation and detection or quantitative analysis for every drift mobility or for approximately every ionic species, but to this end, it is necessary to adjust the timing of the application of a potential to the ion source and the timing of the application of an opening pulse to the ion injection shutters for every ionic species, and a high speed-high resolution pulse measuring circuit must be used.

Further, U.S. Pat. Nos. 3,835,328 and 4,238,678 disclose other apparatuses for detecting trace amounts of impurity gas components in gaseous samples operated at atmospheric pressure.

The apparatus disclosed in U.S. Pat. No. 3,835,328 is mainly provided with a recombination region positioned downstream from an ionization region which is equipped with a radiation source. This recombination region comprises electrically insulating washers fitted into a shaft at proper intervals, each having a hole of a different diameter to form a tortuous path through which the impurity gas ions can pass. The impurity ions pass through the tortuous path while the recombination of the ionic main components of the sample gas is promoted during transfer therethrough. The ions are detected by a screen of an electrically conducing material in a collection region positioned downstream from the recombination region. The shaft is electrically connected to the conductive screen through a DC voltage source and an ammeter arranged in series, and a DC voltage is applied between the shaft and the screen to permit an electric current which corresponds to the concentration of the impurity to be read out.

The detecting apparatus disclosed in U.S. Pat. No. 4,238,678 comprises a first drift region which is defined by a grid and a shutter and which is positioned downstream from an ionization region, and a second drift region which is defined by the shutter and a collector electrode and which is positioned downstream from the shutter. The grid comprises a plurality of conducting materials arranged parallel to one another and is positioned perpendicularly to the flow direction of a sample gas stream. An electric voltage is alternatively applied to the plurality of conducting materials so that each pair of neighboring conducting materials have different potentials at each instance. Thus, the grid serves to collect light ions having a high drift mobility among the ions present and to conduct heavy ions having a low drift mobility to the first drift region. Moreover, the shutter has the same structure and arrangement as the grid and serves to guide specific ions or discrete packets of ions among the low mobility ions which drift through the first drift region to the second drift region. A conductive ring is arranged around the periphery of the first and second drift regions, through which an electric field is established. The field has a desired potential gradient which is parallel to the direction of the sample gas stream containing ions. The drift velocities of ions in the first and second drift regions depend on the foregoing electric field and the ions which drift through the second drift region are collected and detected by a collector electrode positioned at the downstream end of the second drift region.

U.S. Pat. No. 4,119,851 discloses an apparatus for detecting impurities in a gaseous sample which comprises a recombination tube as disclosed in U.S. Pat. No. 3,835,328 and a drift tube as disclosed in U.S. Pat. No. 4,238,678 which are connected in series.

The recombination tube disclosed in U.S. Pat. No. 3,835,328 allows the recombination of main ionic components of a sample gas as soon as possible to remove the same and thus serves to guide only the impurity ions to a detector, while the drift tube disclosed in U.S. Pat. No. 4,238,678 serves to separate and detect impurity ions for all drift mobilities, approximately corresponding to their molecular weights, or for every species of the impurities.

As has been discussed above in detail, all of the conventional apparatuses for detecting impurities in a gas sample are designed in such a manner that only impurity ions are guided to detectors such as collector electrodes. In these apparatuses, it is sufficient that only a part of the impurity ions are involved in the detection, but the ions of the main components of the gas obstruct the detection of the impurity ions.

Furthermore, the grid and shutter disclosed in U.S. Pat. No. 4,238,678 are both realized by arranging a plurality of conductive materials perpendicularly to the flow direction of a sample gas containing ions so that there does not occur any warping in the distance between neighboring pairs of conductive materials and so that a desired electric field can thus be established therebetween. This makes the production of these apparatuses very difficult.

SUMMARY OF THE INVENTION

The present invention has been completed to eliminate the foregoing problems associated with the conventional apparatuses for detecting impurities in a gas sample, and accordingly it is a first object of the present invention to provide a sensor for detecting a high molecular weight substance in which the output of an ion detector and the concentration of a high molecular weight substance, such as a harmful substance present in a sample gas, can be correlated with one another through a principle differing from that utilized in the conventional apparatuses.

It is a second object of the present invention to provide a simple sensor which is particularly suitable for the detection of high molecular weight impurities, having a molecular weight of about 100 or higher, present in a gaseous sample mainly comprising a low molecular weight gas such as air.

It is a third object of the present invention to provide a highly sensitive sensor for detecting and quantitatively analyzing a high molecular weight substance such as a harmful substance present in a gas sample without using strong radiant rays, which sensor is small and lightweight, can be set up at any desired position in a measuring environment, can be portable and can easily be manufactured.

To accomplish the foregoing objects, the present invention provides a sensor for detecting a high molecular weight substance present in a gas sample which comprises an ionization region for ionizing the gas sample containing the high molecular weight substance at atmospheric pressure to form light ions and for ionizing the high molecular weight substance through an ion-molecule reaction between the light ions and the high molecular weight substance to thus form heavy ions, a gas-introduction region for the introduction of the sample gas into the ionizing region, an ion-passage control region which comprises a first electrode having a first fixed electric potential and a second electrode positioned opposite to the first electrode across a gap or interstice, these electrodes establishing an electric field therebetween for controlling the passage of the sample gas, the light ions and the heavy ions being discharged from the ionization region through the interstice, and a collector electrode for collecting the light and heavy ions passing through the ion-passage control region and for outputting an electric signal in proportion to the quantity of the collected electric charges.

The first and second electrodes are arranged to extend in a direction parallel to the flow direction of the sample gas.

The second electrode may be a potential-fixed electrode having a second fixed electric potential, the ion-passage control region may collect the light ions through a drift effect due to an electric field and allow the heavy ions to pass therethrough, and the collector electrode may output an electric signal in proportion to the quantity of heavy ions collected on the electrode.

The second electrode may be a float electrode having a floating potential. The sensor further comprises a third electrode having a second fixed potential and capable of floating the potential of the second electrode between the first fixed potential and the second fixed potential. The ion-passage control region may collect at least part of the light and heavy ions through a drift effect due to an electric field, and the collector electrode may output an electric signal in proportion to the quantity of the light and heavy ions which pass through the ion-passage control region.

The ionization region may be designed so that it simultaneously plays the foregoing role of the third electrode or the third electrode may be positioned in the vicinity of the interface between the ionization region and the ion-passage control region.

In another embodiment, the sensor may be designed such that a potential difference is established between the ionization region and the ion-passage control region or between the first electrode and the collector electrode.

In the sensor according to the present invention, a sample gas such as air is introduced into the ionization region through the gas-introduction region, ionized (primary ionization) by the radiation from the radiation source at atmospheric pressure to form light ions (such as $O_2^+N_2^+$ when the sample gas is air), and the light ions thus formed and a high molecular weight substance present in the sample gas undergo an ion-molecule reaction to ionize (secondary ionization) the high molecular weight molecules and to thus form heavy ions. Then the sample gas, light ions and heavy ions are conducted to the ion-passage control region, where at least part of the ions are deflected by the drift effect of the electric field established between the first electrode having a fixed electric potential and the second electrode when the ions pass through the interstice formed between these electrodes and are collected by the first or second electrode. The ions which are not collected by the first or second electrode pass through the interstice and are collected by the collector electrode. At this stage, if the electric field intensity established between the first and second electrodes is adjusted so that the signal output of the collector electrode corresponds to the concentration of the high molecular weight substance present in the sample gas, the high molecular weight substance can be detected and quantified on the basis of the signal outputted from the collector electrode.

The second electrode may have a fixed potential to fix the intensity and distribution of the electric field established between the first and second electrodes. In this case, the light ions are collected in the ion-passage control region through the drift effect due to the electric field, while the heavy ions pass through the ion-passage control region and are collected by the collector electrode. They are detected and quantified on the basis of the signal outputted from the collector electrode, which is in proportion to the amount of the ions collected.

In the ion-passage control region, on the other hand, the second electrode may be a float electrode having a floating potential. An electric field may be established between the third and first electrodes, each having a fixed potential, and the potential of the float electrode may be maintained at a level between the potentials of the first and third electrodes through the electric field established therebetween to thus indirectly establish an electric field between the first electrode and the second electrode.

When the ions from the ionization region are introduced into the ion-passage control region, the electric potential of the float electrode is determined by the electrostatic capacity between the float and third electrodes, the electrostatic capacity between the float and first electrodes, and the positive and negative charges collected by the float electrode. The electric potential of the float electrode falls within the range between the potential of the third electrode and that of the first electrode. In other words, the charge of the ions which drift toward the float electrode due to the electric field established between the first and float electrodes is opposite to that of the ions which drift toward the float electrode due to the electric field established between the third and float electrodes, and they reach an equilibrium state at a potential observed when the amounts of both charges are equal to one another. The ionic charges collected on the first electrode have a sign opposite to that of the ionic charges collected on the float electrode when the ions pass through the interstice formed between the first and float electrodes.

If the electric potential of the third electrode is set to a level in order to establish the potential of the float electrode at which most of the ions are collected by the first or float electrode when any high molecular weight substance is not present and the polarity of the third electrode is selected such that the ions of high molecular weight substances are drifted from the third electrode to the float electrode, the averaged ionic mass (positive or negative) of the high molecular weight ions increases when s high molecular weight substance is present, the amount of the charges which have the same polarity as that of the high molecular weight ion, drift toward and arrive at the float electrode due to the electric field decreases in proportion thereto, the potential on the float electrode approaches that on the first electrode, which in turn leads to a decrease in the intensity of the electric field established between these electrodes and a reduction in the number of ions collected during the passage thereof through the interstice formed between the first and float electrodes as well as an increase in the number of ions which pass through the interstice.

Thus, if the second electrode is a float electrode, or an electrode having a floating potential, the difference between the effective ionic masses observed in the presence and absence of high molecular weight ions causes a change of the potential of the float electrode and the number of the ions which pass through the ion-passage control region is greatly increased as the potential of the float electrode varies. However, if the potentials of both first and second electrodes are fixed, the number of the ions which pass through the control region is exclusively determined by the drift effect and the difference between the ionic masses. As has been explained above, the potential of the float electrode varies approximately in proportion to the number of high molecular weight ions, and accordingly, the concentration of the high molecular weight substance present in the sample gas can be detected with high sensitivity on the basis of the number of the ions passing through the control region. Thus, the foregoing functions and effects can be ensured if the second electrode is a float electrode. More specifically, in this embodiment, the difference in the drift effect due to the difference between the ionic masses is not used for detection as such, but is used for detection after amplifying the difference through the potential change of the float electrode.

Moreover, a potential difference can be established between the ionizing region and the ion-passage control region to promote the introduction of ions having the same polarity as the heavy ion into the control region, or a potential difference can be established between the first electrode and the collector electrode to enhance the ionic charge-collecting efficiency of the collector electrode.

In this respect, if the first and second electrodes are designed so that they both extend in a direction parallel to the flow direction of the sample gas, the processing accuracy required for the first and second electrodes is relaxed and the interstice between the first and second electrodes can easily be formed.

According to the present patent application, the passage of ions is controlled in an ion-passage control region maintained at a pressure approximately equal to atmospheric pressure. This eliminates the use of a large-scale high vacuum apparatus, the use of which is indispensable to methods which makes use of mass spectrometry, and also permits the radioactivity used for ionization to be reduced. Techniques making use of the flight time separation method are greatly restricted by these factors.

The above and other objects, effects, features and advantages of the present invention will be become more apparent from the following description of embodiments thereof taken in conjunction with the accompanying drawings.

DESCRIPTION OF PREFERRED EMBODIMENTS

The present invention will now be described in detail with respect to the preferred embodiments, and it will be apparent to those skilled in the art that changes and modifications may be made without departing from the invention in its broader aspects, and it is the intention, therefore, in the appended claims to cover all such changes and modifications as fall within the true spirit of the invention. In the accompanying drawings, components or parts which are common in the different embodiments are designated by the same reference numerals and redundant explanations thereof will be omitted.

First Embodiment

Figure 1:
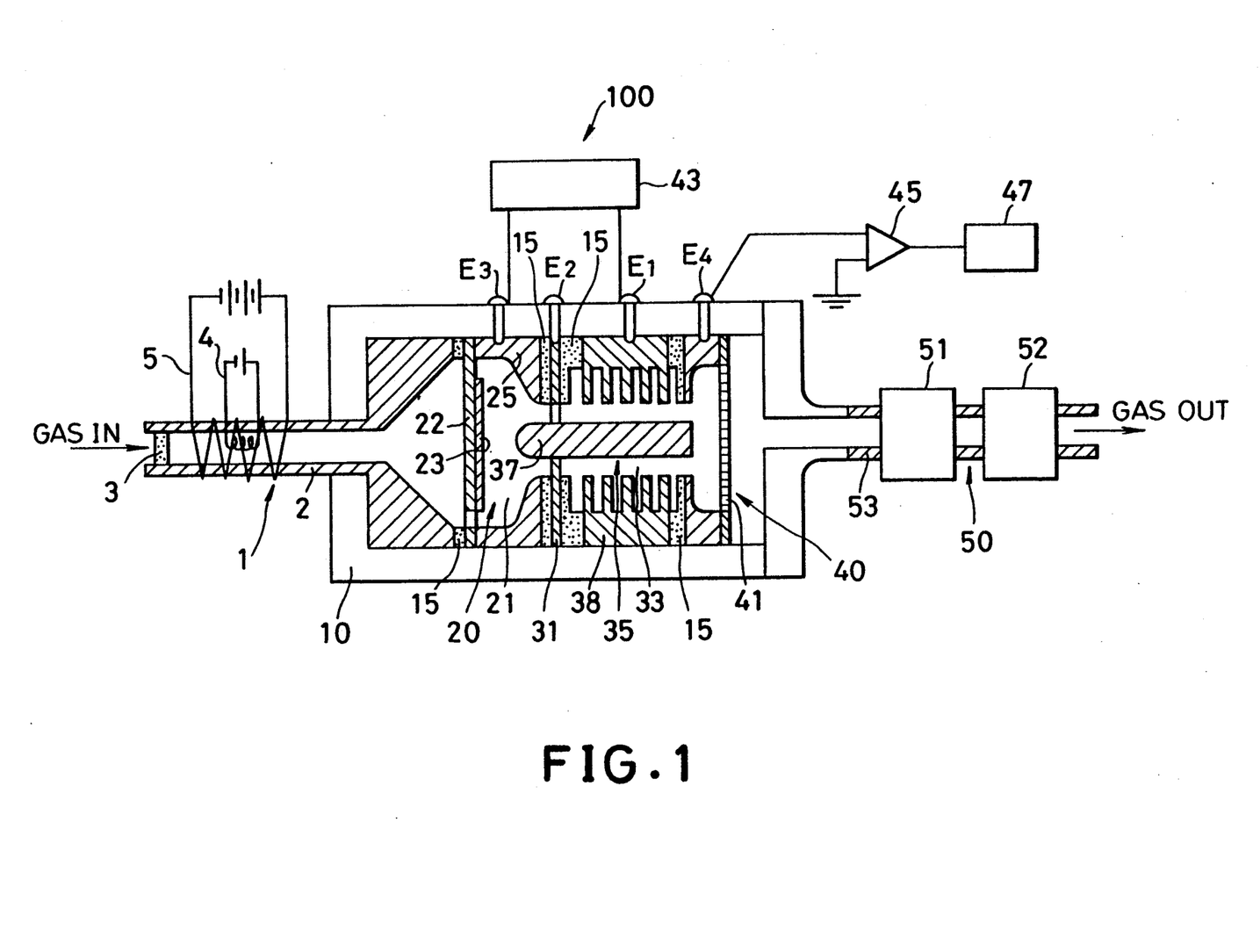
FIG. 1 is a sectional view schematically showing an embodiment of a sensor for detecting a high molecular weight substance according to the present invention, in which a first electrode in an ion-passage control region has a fixed potential, a second electrode has a floating potential, and a third electrode is provided at an ionizing region.

FIG. 1 is a schematic block diagram showing an embodiment of sensor 100 for detecting a high molecular weight substance according to the present invention.

The sensor 100 mainly comprises a gas-introduction region 1, an ionization region 20, an ion-passage control region 35 and a collector electrode region 40. The gas-inlet region 1 comprises an inlet tube 2, a dust removing filter 3, a gas heater 4 and an inlet tube heater 5. The ionization region 20 comprises an internal space 21, a support 22 for a radiation source and a radiation source 23. The ion-passage control region 35 comprises a central electrode 37 supported by a central electrode support 31 and a counter electrode 38 positioned around the central electrode 37 in such a manner that it faces the central electrode 37 across a gap or interstice 33. The collector electrode region 40 mainly comprises a collector electrode 41 disposed approximately perpendicular to a gas flow path.

In FIG. 1, a sample gas (such as air) containing a high molecular weight substance (such as a harmful substance to be detected or measured) is introduced into the ionization region 20 through the inlet tube 2. Dust present in the sample gas is removed by the dust removing filter 3. In order to prevent the adsorption of the high molecular weight substance onto the inner wall of the inlet tube 2, the inlet tube 2 is preferably as short as possible and the sample gas and the inlet tube 2 are preferably heated by the gas heater 4 and the inlet tube heater 5 respectively. The gas heater 4 serves to heat the sample gas to a predetermined temperature to ensure high sensitivity in the detection of the high molecular weight substance and to ensure reliability of the measurement.

The introduction of the sample gas is performed by the aspiration action of a small pump 52 disposed at an exhaust pipe 53. A flow rate controller 51 for controlling the volumetric flow rate or mass flow rate is preferably disposed immediately upstream from the pump 52. Reference numeral 50 stands for a gas-aspiration region, mainly comprising the flow rate controller 51, the pump 52 and the exhaust pipe 53.

The other end of the gas-inlet tube 2 intrudes into a container 10 of the sensor 100, and the inner and outer diameters of the tube 2 are expanded to form the internal space 21 within the container 10. The radiation source 23 supported by the radiation source support 22 is positioned within the internal space 21.

Primary ionization

The sample gas introduced into the ionization region 20 is irradiated by the radiation source 23 and molecules of the main component of the gas are primarily ionized to give light ions. When the sample gas is air, the light ions formed through the primary ionization by the irradiation with the radiation are $O_2^+$, $N_2^+$ or the like. The number of molecules of the high molecular weight substance, contained as an impurity in the sample gas, is very small compared with the number of molecules of the main component thereof, and accordingly the number of high molecular weight molecules that are ionized through the primary ionization is correspondingly very small.

An $\alpha$-ray source such as $^{241}$Am having a high ionization efficiency is preferably used as the radiation source for the primary ionization. However, it is also possible to use a $\beta$-ray source such as $^{63}$Ni, as is currently employed in conventional techniques, without any trouble. In any case, there is no need for collimating the radiation prior to use. For this reason, when $^{241}$Am is selected as the radiation source, it is sufficient to use an intensity on the order of not more than 100 $\mu$Ci, which is one five-hundredth of the 50 mCi of $^{63}$Ni currently employed in the conventional techniques. Accordingly, legal restrictions by the regulations on the handling of radioactive substances are substantially relaxed.

As a further energy source for the primary ionization, a corona discharge between needle electrodes (not shown) may be used in addition to the foregoing radiation rays.

Secondary ionization

The high molecular weight substance present in the sample gas is ionized through an ion-molecule reaction with the light ions formed by the foregoing primary ionization to form heavy ions. In the present invention, ions having a molecular weight of less than 100 are referred to as "light ions", while those having a molecular weight of not less than 100 are referred to as "heavy ions". A heavy ion has a lifetime longer than that of a nitrogen or oxygen ion, so even if the high molecular weight substance is present in the air at a molecular concentration of only 1 ppm with respect to the molecules of the air component, the number of light ions that are present is approximately on the same order as the number of heavy ions that are present when the light and heavy ions are ready for introduction into the ion-passage control region, as will be explained below.

The light and heavy ions formed in the ionization region 20, as well as the sample gas that has not been ionized, are drawn in the ion-passage control region 35 positioned immediately behind the ionization region 20. The ion-passage control region 35 comprises the central electrode 37 supported by the central electrode support 31 and the counter electrode 38 positioned around the central electrode 37 in such a manner that it faces the central electrode 37 across the interstice 33.

In FIG. 1, the central electrode 37 is a "float" electrode having a floating potential, and will occasionally be called the second electrode. The counter electrode 38 is kept at a fixed potential and will occasionally be called the first electrode. The ionization region 20 simultaneously serves as a further electrode having a fixed potential, in that a third electrode 25 is disposed at the ionization region 20. Thus, an electric field having a desired intensity is established between the third electrode 25 and the first electrode 38. This electric field serves to float the potential on the float electrode 37 between the voltages on the first electrode 38 and the third electrode 25. The interface between ion-passage control region 35 and ionization region 20 is insulated and the tip of central electrode 37 or the float electrode is exposed within internal space 21 in order to facilitate the collection of ions having the same polarity as that of the heavy ions. The collector electrode region 40 is positioned immediately behind the ion-passage control region 35 and mainly comprises the collector electrode 41, which is disposed approximately perpendicular to a gas flow path. The collector electrode 41 has a fine mesh in order to increase the frequency of collision with ions and to increase the field intensity in the vicinity of the mesh. The heavy ions which pass through ion-passage control region 35 are collected by the collector electrode 41. They transfer their charges to the collector electrode 41 and are converted into neutral molecules and discharged. The collector electrode 41 outputs a signal current which is proportional to the quantity of the charges collected. This signal current is received by a preamplifier 45 which drives a display/record portion 47. The display/record portion 47 comprises a displayer or a recorder or an appropriate combination thereof and indexes, displays or records the results of the detection or quantification of the high molecular weight substance on the basis of the output signal from the collector electrode 41.

Reference numeral 43 in FIG. 1 represents a DC power supply for applying fixed electric potentials E1 and E3 to the first electrode 38 and the third electrode 25 respectively. In the sensor 100 shown in FIG. 1, DC power supply 43 is not connected to the second electrode 37, whose voltage $E_2$ is a floating voltage. A voltage approximately equal to the earth voltage (i.e., ground) is applied to the collector electrode 41.

A potential difference $E_3 - E_1$ having a proper magnitude is established between the first electrode 38 and the third electrode 25. Thus, a potential gradient can be established. The polarity of the potential difference is selected so that ions from the ionization region 20 having the same polarity as that of the heavy ions are deflected toward the float electrode 37. Thus, the potential of the float electrode 37 and the central electrode support 31 is such that ions from the ionization region 20 having the same polarity as the heavy ions are deflected toward the central electrode or float electrode 37, while the polarity of the electric field established in the interstice 33 between the float electrode 37 and the first electrode or counter electrode 38 is such that ions having a polarity opposite to that of the heavy ions are deflected toward the float electrode 37.

In this condition, ions having the same polarity as the heavy ions are fed from the ionization region 20 to the float electrode 37, while those having a polarity opposite to that of the heavy ions are fed thereto through the interstice 33. The potential of the float electrode 37 gradually reaches a level at which the quantity of charges of both minus and plus signs fed to the float electrode are balanced with one another, and stabilized at that potential. At this stage, when the rate of the heavy ions in the sample gas increases, the number of ions having the same sign as the heavy ions fed to the float electrode 37 correspondingly decreases and the potential of the float electrode approaches that of the counter electrode 38 since the drift effect due to the heavy ions is smaller than that attained by the light ions. This results in a reduction of the intensity of the electric field established within the interstice 33 and in turn a lowering of the drift effect due to the electric field established in the interstice 33, so that the number of ions which pass through the interstice 33 and the quantity of charges collected by the collector electrode 4; increase.

More specifically, the number of the heavy ions in the sample gas plays the role of an amplifier by affecting the electric potential of the central electrode 37 to thus cause a shift of the signal current. When the fixed potential of the third electrode is selected, in advance, so that the potential on the float electrode is set to a level at which most of the ions can be collected due to the drift effect when no high molecular weight substance is present and the polarity of the potential on the third electrode is selected so that any high molecular weight ions are drifted from the third electrode to the float electrode, the foregoing amplification effect can be effectively induced.

When the amplification effect is induced, the ion-collecting effect in the ion-passage control region 35 is somewhat weakened, and not only the heavy ions but also a part of the light ions introduced into the interstice 33 pass therethrough and the charges thereof are collected by the collector electrode 41. Thus, if the potentials of both the first and third electrodes are adjusted in such a manner that a proper correlation is established between the heavy ion concentration in the sample gas and the signal current outputted from the collector electrode 41, the high molecular weight substance can be detected or quantified.

As shown in FIG. 1, the central electrode 37 and the counter electrode 38 are preferably long electrodes laterally extending along the flow direction of the sample gas containing ions. When the central electrode 37 and the counter electrode 38 are designed to have the structure and arrangement discussed above in detail, the processing and assembly of these electrodes can be substantially simplified, the interstice 33 can easily be established, and the desired dimensional precision thereof can easily be ensured. Incidentally, the sensor for detecting a high molecular weight substance shown in FIG. 1 is designed so that the central electrode 37 has a smooth surface and so that the counter electrode 38 has a baffle structure, but the counter electrode may have a smooth surface.

An alarm means may be connected to display/record portion 47 to give a warning when the level of the high molecular weight substance in the sample gas exceeds a critical point or a predetermined harmful level from the operational standpoint or to stop the operation of machinery and tools which are at work. Moreover, the signals from the collector electrode 41 may be inputted to an information processing device to perform collection, accumulation and statistical processing of data obtained during monitoring or to properly use the data according to need, for instance, to use these data for process management.

Second Embodiment

A sensor 200 for detecting a high molecular weight substance according to the present invention will now be explained in detail with reference to FIG. 2 and Table 1. In this sensor 200, two electrodes in an ion-passage control region, i.e., a central electrode and a counter electrode, are fixed electrodes having fixed potentials. For the sake of simplicity, FIG. 2 uses the same reference numerals used in FIG. 1 to represent the same parts employed in FIG. 1 and having the same functions.

Figure 2:
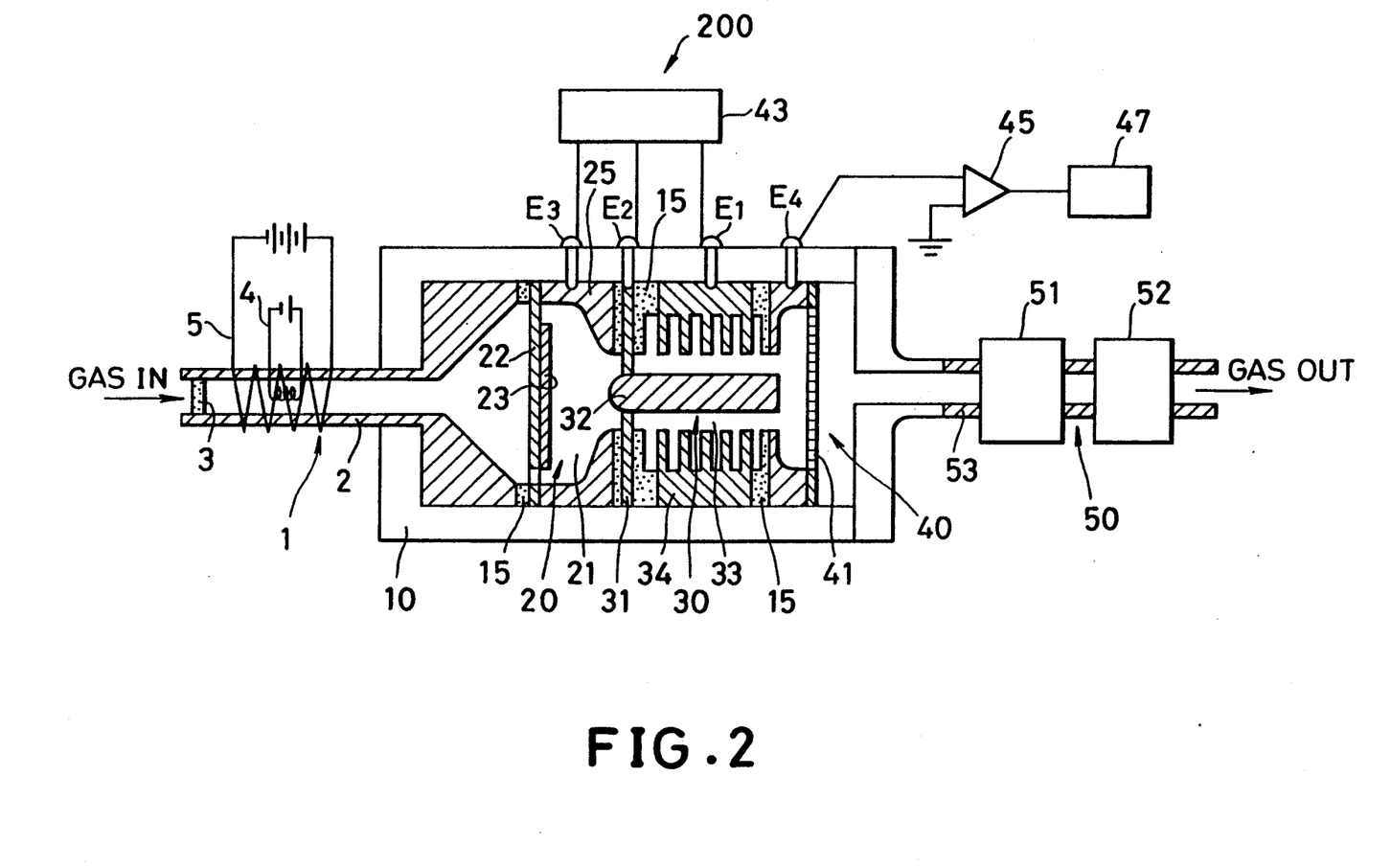
FIG. 2 is a sectional view schematically showing another embodiment of a sensor for detecting a high molecular weight substance according to the present invention, in which first and second electrodes in an ion-passage control region each has a fixed potential.

In FIG. 2, the sensor 200 has the same structure as the sensor 100 shown in FIG. 1 except that a central electrode 32 and a counter electrode 34 in an ion-passage control region 30 are fixed electrodes having fixed potentials. An electric field of a proper intensity is directly established between the central and counter electrodes 32 and 34.

In FIG. 2 and Table 1, $E_1$, $E_2$, $E_3$ and $E_4$ potentials on the counter electrode 34, the central electrode 32, the ionization region 20 and the collector electrode 41, respectively.

Light ions, heavy ions and a sample gas are drawn into the ion-passage control region 30 and pass through the interstice 33 at a speed higher than that observed in the remaining portion of the gas flow path, since the interstice serving as a gas flow path is narrowed down compared with the remaining gas flow path. However, the orbits of the ions (in particular, the light ions) are deformed due to the electric field established between the central and counter electrodes 32 and 34, and as a result the ions are attracted by and adsorbed on the central electrode 32 of the counter electrode 34 and are converted into neutral molecules through the transfer of the charges thereof to the electrodes.

On the other hand, the heavy ions are likewise attracted by the electrode, but most of the heavy ions can be conducted to the collector electrode region 40 positioned immediately behind the ion-passage control region 30 if the intensity of the electric field, the distance and width of the interstice 33, and the flow rate of the gas are properly selected on the basis of the presumed mass of the high molecular weight substance to be detected.

Table 1 shows the experimental results obtained when air containing 0.16 ppm of diethyl phosphite (molecular weight 139) was used as a sample gas and the diethyl phosphite present in the sample gas was detected by the sensor 200 for the detection of a high molecular weight substance under typical factors and conditions.

TABLE 1

| Element | Example 1 | | Example 2 | | Example 3 | |
|---|---|---|---|---|---|---|
| Parameters | | | | | | |
| Sample Gas | Air with 0.16 ppm of Diethyl phosphite, T:22° C., RH:23% | | Air with 0.16 ppm of Diethyl phosphite, T:22° C., RH:23% | | Air with 0.16 ppm of Diethyl phosphite, T:22° C., RH:80% | |
| Gas Inlet Pipe Heater 4 | Sample Gas Temperature after Heating 50° C. | | Sample Gas Temperature after Heating 50° C. | | Sample Gas Temperature after Heating 50° C. | |
| Radiation Source Support 22 | — | Bias Voltage ($E_3$-$E_1$) | — | Bias Voltage ($E_2$-$E_1$) | — | Bias Voltage ($E_3$-$E_1$) |
| Radiation Source 23 | $^{241}$Am α-ray 80 μCi | 7.5 V | $^{241}$Am α-ray 80 μCi | 7.5 V | $^{241}$Am α-ray 80 μCi | 7.5 V |
| Center Electrode Support 31 | — | Bias Voltage ($E_2$-$E_1$) | — | Bias Voltage ($E_2$-$E_1$) | — | Bias Voltage ($E_2$-$E_1$) |
| Center Electrode 32 | 5 mm φ × 12 mmL | 0.5 V | 5 mm φ × 12 mmL | 1.0 V | 5 mm φ × 12 mmL | 1.0 V |
| First Electrode 34 | Inner Dia. 6 mm & 18 mm | Bias Voltage ($E_1$-$E_4$) | Inner Dia. 6 mm & 18 mm | Bias Voltage ($E_1$-$E_4$) | Inner Dia. 6 mm & 18 mm | Bias Voltage ($E_1$-$E_4$) |
| Collector Electrode 41 | Net Structure | 0V | Net Structure | 0V | Net Structure | 0V |
| Flow Rate Controller 51 | Mass Flow Rate Controller | Flow Rate 2 litter/min | Mass Flow Rate Controller | Flow Rate 2 litter/min | Mass Flow Rate Controller | Flow Rate 2 litter/min |
| Result | | | | | | |
| Background Current B | 42 pA | | 18 pA | | 19 pA | |
| Signal + Background Current S | 89 pA | | 50 pA | | 58 pA | |
| Signal Rise Time Constant | Less than 5 sec | | Less than 5 sec | | Less than 5 sec | |
| Signal Falling Time Constant | 30 sec | | 30 sec | | 30 sec | |

T: Temperature,
RH: Relative Humidity

In addition, when the voltage applied between the central electrode 32 and the counter electrode 34 was varied in the Examples shown in Table 1, the following experimental facts were observed (where $V_1$ and $V_2$ represent different values of the voltage between electrodes 32 and 34):

(i) When $V_1$ was greater than $V_2$, the background signal current was abruptly decreased and the net current value due to the heavy ions (ions of diethyl phosphite) was also reduced. In other words, the number of the heavy ions which passed through the interstice 33 was likewise reduced.

(ii) When $V_1$ was, on the contrary, lower than $V_2$, the background current (the signal current due to the light ions) was abruptly increased and correspondingly the net current due to the heavy ions and the background current was increased. In other words, the number of the light ions which passed through the interstice 33 was increased.

These experimental facts clearly indicate that, according to the sensor 200, a sufficient number of heavy ions is formed in the ionization region by primary ionization and subsequent secondary ionization and these ions are guided to the ion-passage control region. Moreover, it is clear that heavy ions can effectively be collected by the collector electrode if various factors and conditions in the ion-passage control region are appropriately selected.

From the foregoing, the following conclusions can be deduced.

i) In the ionization region 20, a trace amount of a high molecular weight substance contained in air is effectively converted into heavy ions on the basis of the principle of the atmospheric pressure ionization method and most of the light ions formed from the air components are neutralized before they are introduced into the ion-passage control region.

ii) In the ion-passage control region 30, the heavy ions are separated from the light ions in a highly efficient manner, although the region is under a pressure approximately equal to the atmospheric pressure, and the signal due to the heavy ions can be extracted by the collector electrode 41 positioned behind the control region.

iii) The foregoing functions i) and ii) of the ionization and ion-passage control regions are likewise ensured when air having a high moisture content is used as a sample gas.

By way of comparison, various factors and conditions for the sensor 100 are listed in the following Table 2.

Figure 3:
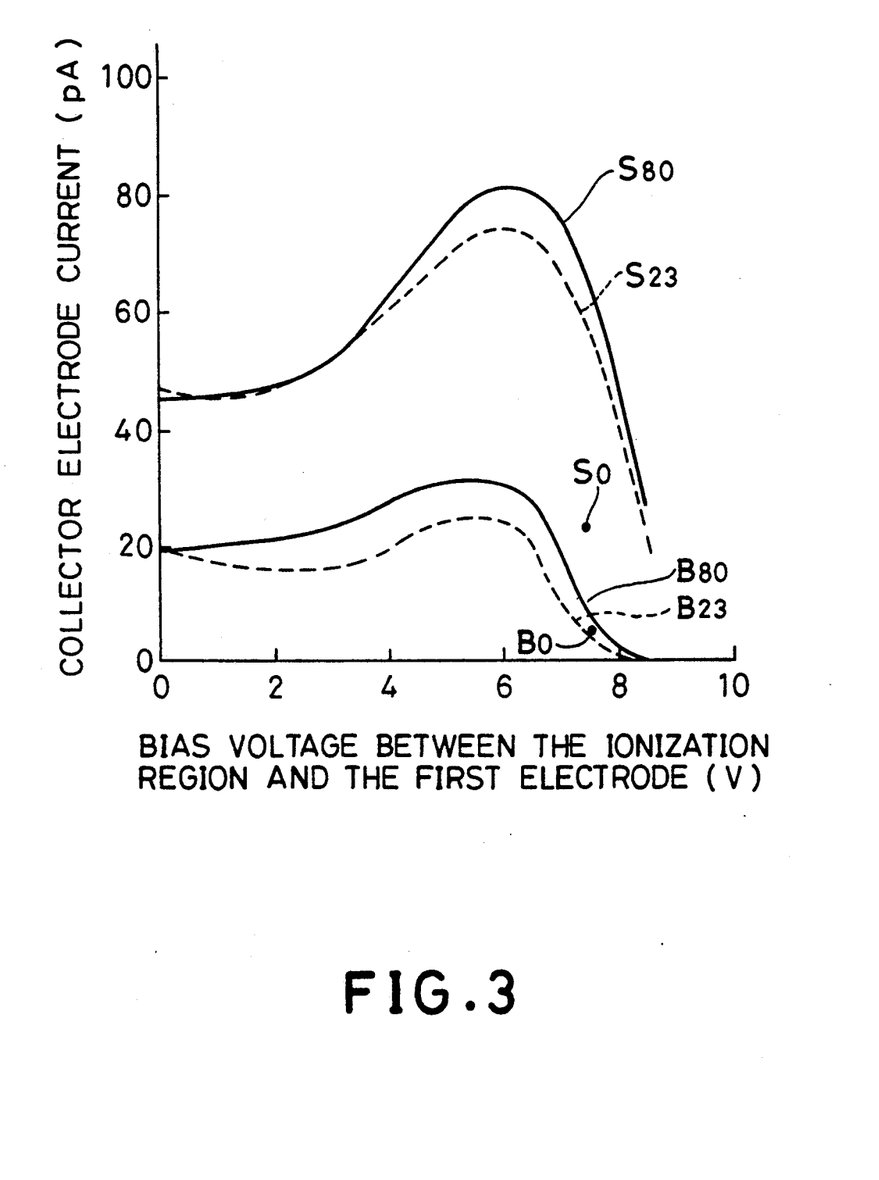
FIG. 3 is a graph illustrating the relation of the voltage between the third electrode having a fixed potential and the first electrode having a fixed potential to the collector electrode current in the sensor shown in FIG. 1.

0.16 ppm of diethyl phosphite at different humidities. In FIG. 3, $S_{23}$ and $S_{80}$ represent signal current curves obtained at humidities of 23% and 80% respectively (the diethyl phosphite content was 0.16 ppm in both cases), while $B_{23}$ and $B_{80}$ represent background current curves observed when the humidities of the sample gas were 23% and 80% respectively. The temperature of the air was 22° C. in both cases. This figure clearly indicates that high ratios of the signal current due to diethyl phosphite to the background current can be obtained when the voltage between the third and first electrodes ranges from 7 to 8.5 V.

Figure 4:
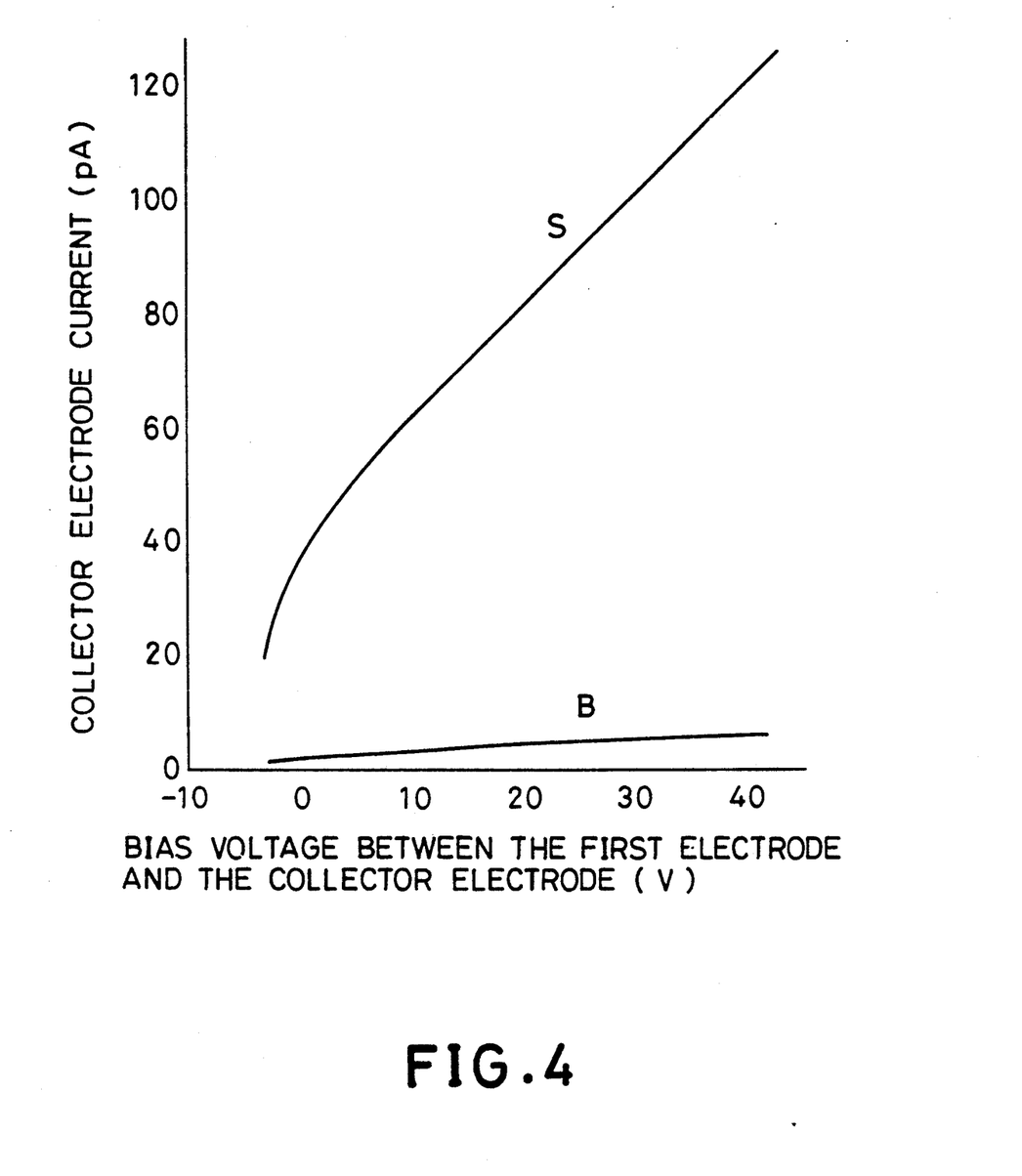
FIG. 4 is a graph illustrating the relation of the voltage between the first electrode and the collector electrode to the collector electrode current in the sensor shown in FIG. 1.

FIG. 4 is a graph illustrating the relation between the collector electrode current and the voltage between the first or counter electrode and the collector electrode 41, which serves as a reference electrode, of the sensor 100 shown in FIG. 1. In FIG. 4, S represents the signal current due to diethyl phosphite (concn. 0.16 ppm) and B represents the background current. Both the signal current and the background current linearly increase at a voltage of 8 V or higher. In this case, the central electrode is a float electrode and other conditions for the measurement illustrated in FIG. 4 are an $E_3-E_1$ of 7.5 V; an air temperature of 22° C.; and a humidity of 23%. In other words, the example shown in FIG. 4 corresponds to Example 4 listed in Table 2 wherein $E_3-E_1$ is fixed to 7.5 V and $E_1-E_4$ is varied.

The following conclusions can be derived from the results shown in FIGS. 3 and 4:

1) When the sample gas contains diethyl phosphite, the ratio of collector electrode current S to background current B is great. This results from the fact that the central electrode comprises a float electrode. The ratio S/B is great in particular when the potential difference between the ionization region 20 and the counter electrode 38 ranges from 7 to 8.5 V.

2) The influence of humidity on the detection is rather low.

3) The signal output S due to high molecular weight substances can be amplified by applying a proper bias voltage between the first electrode (the counter elec-

TABLE 2

| Element | Example 4 | | Example 5 | |
|---|---|---|---|---|
| | Parameters | | | |
| Sample Gas | Air with 0.16 ppm of Diethyl phosphite, T:22° C., RH:23% | | Air with 0.16 ppm of Diethyl phosphite, T:22° C. RH:80% | |
| Gas Inlet Pipe Heater 4 | Sample Gas Temperature after Heating 50° C. | | Sample Gas Temperature after Heating 50° C. | |
| Radiation Source Support 22 | — | Bias Voltage ($E_3-E_1$) | — | Bias Voltage ($E_3-E_1$) |
| Radiation Source 23 | $^{241}$Am α-ray 80 μCi | 0~10 V :Variable | $^{241}$Am α-ray 80 μCi | 0~10 V :Variable |
| Center Electrode Support 31 | — | Bias Voltage ($E_2-E_1$) | — | Bias Voltage ($E_2-E_1$) |
| Center Electrode 37 | 5 mm φ × 12 mmL | Floating | 5 mm φ × 12 mmL | Floating |
| First Electrode 38 | Inner Dia. 6 mm & 18 mm | Bias Voltage ($E_1-E_4$) | Inner Dia. 6 mm & 18 mm | Bias Voltage $E_1-E_4$) |
| Collector Electrode 41 | Net Structure | 0V | Net Structure | 0V |
| Flow Rate Controller 51 | Mass Flow Rate Controller | Flow Rate 2 litter/min | Mass Flow Rate Controller | Flow Rate 2 litter/min |
| | Result | | | |
| | $S_{23}$ & $B_{23}$ in FIG. 3 | | $S_{26}$ & $B_{26}$ in FIG. 3 | |

T: Temperature.
RH: Relative Humidity

FIG. 3 is a graph illustrating the relation between the collector electrode current and the voltage between the third electrode and the first electrode of the sensor 100 shown in FIG. 1. The sample gas was air containing trode) and the collector electrode.

Figure 5:
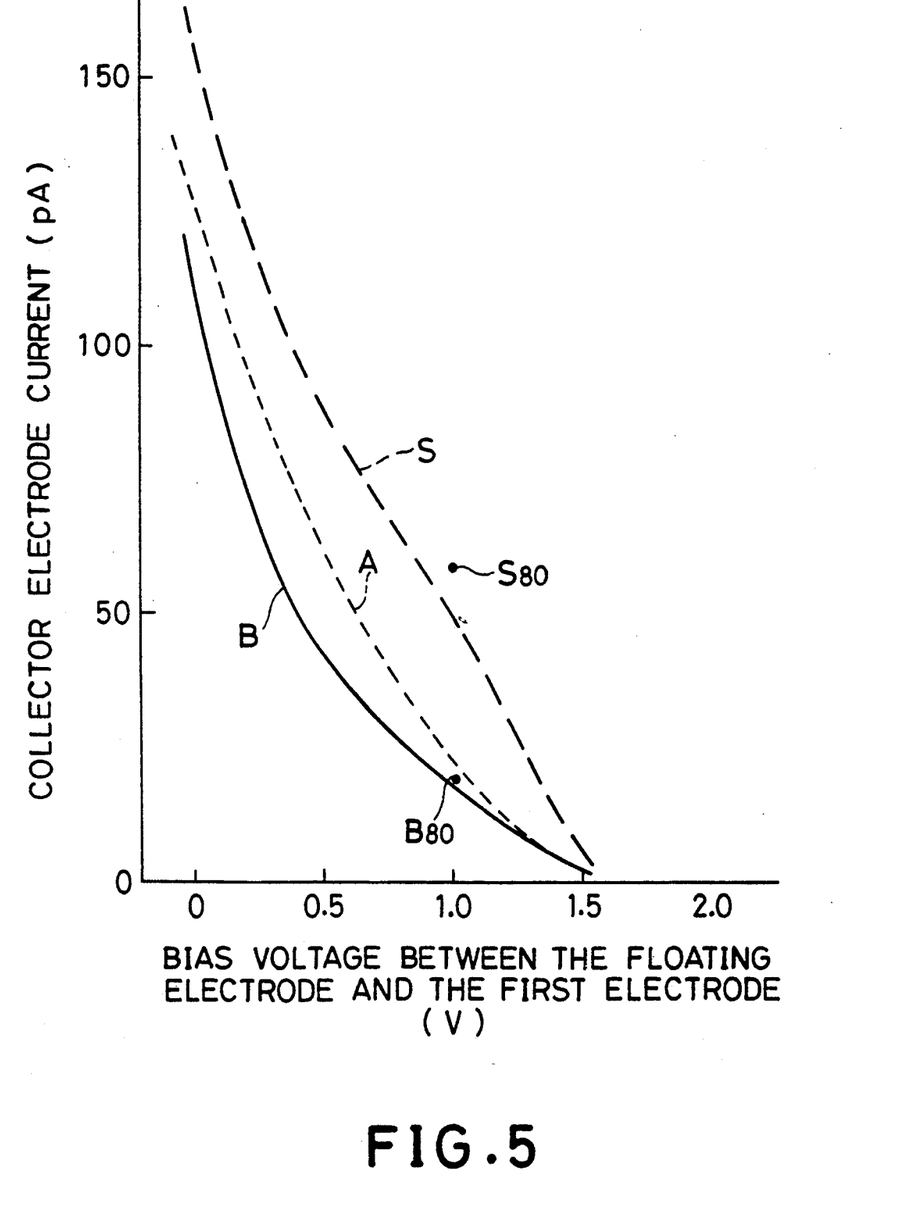
FIG. 5 is a graph illustrating the relation of the voltage between the second electrode as the float electrode and the first electrode and the collector electrode current, which is observed when an external voltage is applied to the float electrode of the sensor shown in FIG. 1.

FIG. 5 is a graph illustrating the relation between the collector electrode current and the voltage between a float electrode and a first electrode (electrode having a fixed potential) determined at 22° C. by the sensor listed in Table 2 when an external voltage is applied to the central electrode 37 as a float electrode using a dried air (dew point −40° C.) and an air having a humidity of 23% ($E_3 - E_1$ is fixed to 7.5 V). In FIG. 5 the potential difference between the central electrode and the counter electrode, which is taken as a reference, is plotted on the abscissa and the collector electrode current is plotted on the ordinate Any difference in the collector electrode current is not observed between cases in which the dried air per se and the air containing 0.16 ppm of diethyl phosphite are used and they give a single curve A. At this stage, however, when the potential of the central electrode is set free (floated), the background current Be becomes 5 pA, while the signal current Se due to diethyl phosphite (concn. 01.6 ppm) becomes 23 pA (see FIG. 3). Thus, the detection of diethyl phosphite can be ensured.

Curves S and B in FIG. 5 were obtained using air having a humidity of 23%, the former being a signal current curve observed for air containing 0.16 ppm of diethyl phosphite and the latter being a background current curve. Points $B_{80}$ and $S_{80}$ appearing in the same figure represent a background current value obtained for an air sample having a humidity of 80% and a signal current value observed for an air sample containing 0.16 ppm of diethyl phosphite and having a humidity of 80%. These data indicate that the background current signal is clearly separated from the signal current due to the high molecular weight substance when the humidity of the sample gas exceeds a certain level. While not wanting to be bound by any particular theory, it is believed that if water molecules are present in a sample gas, water molecules ionized through the primary ionization promote deionization of once formed ions of the air components and contribute to the formation of polymer ions during the secondary ionization process.

The following conclusions can be derived from the foregoing:

a) When the central or second electrode is a float electrode, high molecular weight substances can be detected with a substantially improved sensitivity.

b) When characteristics as shown in FIG. 5 can be obtained, the 0 point compensation can be ensured by applying an external voltage to the float electrode or by temporarily converting the float electrode into an electrode having a fixed potential.

Figure 6:
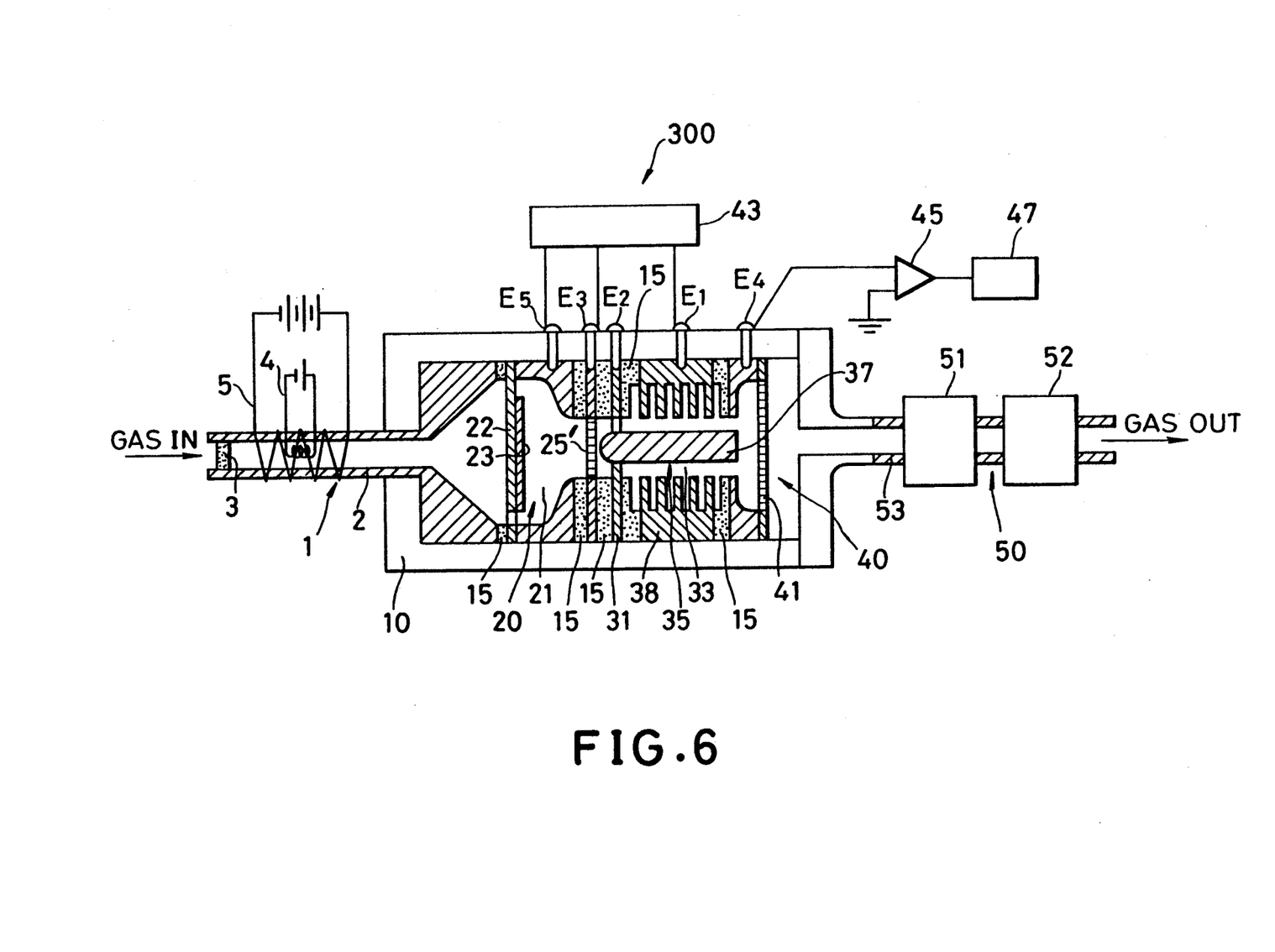
FIG. 6 is a sectional view schematically showing a further embodiment of a sensor for detecting a high molecular weight substance according to the present invention, in which a third electrode having a fixed potential is arranged separately from an ionization region.

Although the third electrode 25 at the ionization region 20 of the sensor 100 serves as a fixed electrode having a fixed potential, a separate third electrode 25' may be positioned between the ionization region 20 and the ion-passage control region 30 as shown in FIG. 6. In this case, a terminal for imparting a potential $E_6$ to the ionization region 20 is provided along with a terminal for applying a potential $E_3$ to the third electrode 25'. In FIG. 6, reference numeral 15 represents an insulating material.

In the foregoing description, embodiments in which the central electrode is a float electrode and the counter electrode is a fixed electrode have been discussed, but is also possible to design the sensor so that the counter electrode is a float electrode and the central electrode is a fixed electrode. In this case, however, one end of the counter electrode is instead exposed within internal space 21, unlike the apparatus shown in FIG. 1.

Incidentally, the internal walls of the sensors 100, 200 and 300 may be contaminated with impurities, but the impurities adhered to these sensors can be removed by attaching a stop valve to the gas-inlet tune 2, connecting a bypass pipe having a built-in high performance filter to a portion of the gas-inlet tube 2 between the stop valve and the container 10, closing the stop valve to block the sample gas, supplying a cleaning gas such as clean air to the sensor 100, 200 or 300 through the bypass pipe, or providing a heater, around the outer periphery of container 10, for heating the part of the sensor accommodated in the container to heat the sensor at a high temperature, or any combination of these means.

As has been explained above, the sensor for detecting a trace amount of high molecular weight substance present in a sample gas according to the present invention comprises a gas-inlet or gas-introduction region for introducing the sample gas into the sensor; an ionization region positioned behind the gas-introduction region and provided with an ionization means such as a radiation source or a discharge mechanism, the region ionizing the sample gas introduced through the gas-introduction region by the action of the ionization means under atmospheric pressure to form light ions and then ionizing the high molecular weight substance through an ion-molecule reaction between the light ions and the high molecular weight substance to thus give heavy ions; an ion-passage control region positioned behind the ionization region and provided with a first electrode and a second electrode which is positioned opposite to the first electrode across a gap or interstice and which establishes an electric field within the interstice together with the first electrode, the control region controlling the passage of the heavy ions and light ions through the action of the electric field established between the first and second electrodes; and a collector electrode positioned behind the ion-passage control region, capable of collecting charges of the ions which pass through the ion-passage control region and outputting a signal in proportion to the quantity of ionic charges collected, wherein the first electrode is an electrode having a fixed potential, the second electrode is a float electrode and a third electrode is provided to establish an electric field of a fixed intensity between the third and first electrodes so that the potential on the float electrode is indirectly controlled by a voltage applied to the third electrode or on the basis of the drift effect of the electric field established between the first and second electrodes each having a fixed potential. Thus, charges can pass through the ion-passage control region in an amount corresponding to the concentration of the high molecular weight substances.

As discussed above, the present invention makes it possible to indirectly or directly adjust the intensity of the electric field established within the interstice formed between the first and second electrodes under a pressure approximately equal to atmospheric pressure Therefore, the collector electrode can easily collect ions whose amount corresponds to the concentration of the high molecular weight substances, and the detection sensitivity is substantially improved compared with that achieved by a sensor in which the intensity of the electric field established within the interstice formed between the first and second electrodes is fixed. Furthermore, the sensor has a simple structure and can easily be manufactured. It is also suitable for carrying or for portable use.

In the sensors shown in FIGS. 1, 2 and 6, the central electrode 32 or 37 has a smooth surface while the counter electrode 34 or 38 has a baffle structure, but the counter electrode may likewise have a smooth surface. This structure provides an advantage in that a uniform electric field distribution is ensured between the central and counter electrodes. However, if both or either of the surfaces of the central and counter electrodes are roughened or at least one of these is designed to have a baffle structure, an electric field having a high intensity can be established in the vicinity of the electrode having a baffle structure and thus an improved ion-collection effect can be anticipated.

What is claimed is:

1. A sensor for detecting a high molecular weight substance present in a gas sample, comprising:
    an ionization region for ionizing the gas sample containing the high molecular weight substance at atmospheric pressure to form light ions and for ionizing the high molecular weight substance through an ion-molecule reaction between the light ions and the high molecular weight substance to thus form heavy ions;
    a gas-introduction region for introducing the sample gas into said ionization region;
    an ion-passage control region including a first electrode having a first fixed electric potential and a second electrode having a floating electric potential, said second electrode being positioned opposite to said first electrode across an interstice, an electric field being established between said first and second electrodes for controlling the passage of the sample gas, the light ions and the heavy ions discharged from said ionization region through said interstice;
    a collector electrode for collecting the light and heavy ions passing through said ion-passage control region; and
    a third electrode having a second fixed electric potential for floating the potential of the second electrode between the first fixed potential and the second fixed potential,
    wherein said ion-passage control region collects at least a part of the light and heavy ions through the drift effect of the electric field, and
    wherein said collector electrode outputs an electric signal in proportion to the quantity of the light and heavy ions which pass through said ion-passage control region.

2. A sensor as claimed in claim 1, wherein said first and second electrodes are arranged and extend along a direction parallel to the flow direction of the sample gas.

3. A sensor as claimed in claim 2, wherein a potential difference is established between said ionization region and said ion-passage control region for promoting the introduction of ionic charges having the same polarity as that of the heavy ions into said ion-passage control region.

4. A sensor as claimed in claim 2, wherein a potential difference is established between said first electrode and said collector electrode for improving the ion-collecting efficiency.

5. A sensor as claimed in claim 1, wherein a potential difference is established between said ionization region and said ion-passage control region for promoting the introduction of ionic charges having the same polarity as that of the heavy ions into said ion-passage control region.

6. A sensor as claimed in claim 1, wherein a potential difference is established between said first electrode and said collector electrode for improving the ion-collecting efficiency.

7. A sensor as claimed in claim 1, wherein said third electrode is positioned between said ionization region and said ion-passage control region.

8. A sensor as claimed in claim 7, wherein a potential difference is established between said ionization region and said ion-passage control region for promoting the introduction of ionic charges having the same polarity as that of the heavy ions into said ion-passage control region.

9. A sensor as claimed in claim 7, wherein a potential difference is established between said first electrode and said collector electrode for improving the ion-collecting efficiency.

10. A sensor as claimed in claim 7, further comprising an additional electrode disposed at said ionization region, said additional electrode having a fixed electric potential.

11. A sensor for detecting a high molecular weight substance present in a gas sample, comprising:
    an ionization region for ionizing the gas sample containing the high molecular weight substance at atmospheric pressure to form light ions and for ionizing the high molecular weight substance through an ion-molecule reaction between the light ions and the high molecular weight substance to thus for heavy ions;
    a gas-introduction region for the introduction of the sample gas into said ionization region;
    an ion-passage control region including a first electrode having a first fixed electric potential and a second electrode positioned opposite to said first electrode across an interstice, said first and second electrodes establishing an electric field therebetween for controlling the passage of the sample gas, the light ions and the heavy ions discharged from said ionization region through said interstice; and
    a collector electrode for collecting the light and heavy ions passing through said ion-passage control region and for outputting an electric signal in proportion to the quantity of the collected electric charge,
    wherein said ionization region simultaneously serves as a third electrode having a second fixed electric potential.

12. A sensor as claimed in claim 11, wherein a potential difference is established between said ionization region and said ion-passage control region for promoting the introduction of ionic charges having the same polarity as that of the heavy ions into said ion-passage control region.

13. A sensor as claimed in claim 11, wherein a potential difference is established between said first electrode and said collector electrode for improving the ion-collecting efficiency.

14. A sensor for detecting a high molecular weight substance present in a gas sample, comprising:
    an ionization region for ionizing the gas sample containing the high molecular weight substance at atmospheric pressure to form light ions and for ionizing the high molecular weight substance through an ion-molecule reaction between the light ions and the high molecular weight substance to thus form heavy ions;

a gas-introduction region for introducing the sample gas into said ionization region;

an ion-passage control region including a first electrode having a first fixed electric potential and a second electrode having a floating electric potential, said second electrode being positioned opposite to said first electrode across an interstice, said first and second electrodes establishing an electric field therebetween for controlling the passage of the sample gas, the light ions and the heavy ions discharged from said ionization region through said interstice;

a collector electrode for collecting the light and heavy ions passing through said ion-passage control region;

a third electrode having a second fixed electric potential for floating the potential of said second electrode between the first fixed potential and the second fixed potential; and a fourth electrode having a fixed electric potential for floating the potential of said second electrode in cooperation with said third electrode, said fourth electrode being separated from said third electrode and being arranged so that said third electrode is between said fourth electrode and said second electrode, wherein said ion-passage control region collects at least a part of the light and heavy ions through the drift effect of the electric field, and wherein said collector electrode outputs an electric signal in proportion to the quantity of the light and heavy ions which pass through said ion-passage control region.

15. A sensor as claimed in claim 14, wherein a potential difference is established between said ionization region and said ion-passage control region for promoting the introduction of ionic charges having the same polarity as that of the heavy ions into said ion-passage control region.

16. A sensor as claimed in claim 14, wherein a potential difference is established between said first electrode and said collector electrode for improving the ion-collecting efficiency.

* * * * *